(12) United States Patent
Kute et al.

(10) Patent No.: US 8,785,432 B2
(45) Date of Patent: Jul. 22, 2014

(54) PHARMACEUTICAL COMPOSITIONS OF AMLODIPINE AND VALSARTAN

(75) Inventors: Anirudha Bhagirath Kute, Pune (IN); Nikhil Prabhakar Malewar, Pune (IN); Makarand Krishnakumar Avachat, Pune (IN)

(73) Assignee: Lupin Limited, Mumbai, Maharashtra (IN)

( * ) Notice: Subject to any disclaimer, the term of this patent is extended or adjusted under 35 U.S.C. 154(b) by 797 days.

(21) Appl. No.: 12/810,662

(22) PCT Filed: Feb. 21, 2008

(86) PCT No.: PCT/IN2008/000103
§ 371 (c)(1),
(2), (4) Date: Jun. 25, 2010

(87) PCT Pub. No.: WO2009/084003
PCT Pub. Date: Jul. 9, 2009

(65) Prior Publication Data
US 2010/0272801 A1 Oct. 28, 2010

(30) Foreign Application Priority Data
Dec. 31, 2007 (IN) .......................... 1449/KOL/2007

(51) Int. Cl.
*A61K 31/54* (2006.01)
*A01N 43/40* (2006.01)

(52) U.S. Cl.
USPC .................. 514/222.8; 514/222.2; 514/222.5; 514/354; 514/356

(58) Field of Classification Search
USPC .................. 514/222.2, 222.5, 222.8; 424/465
See application file for complete search history.

(56) References Cited

U.S. PATENT DOCUMENTS

| | | |
|---|---|---|
| 4,572,909 A | 2/1986 | Campbell et al. |
| 4,879,303 A | 11/1989 | Davison et al. |
| 5,399,578 A | 3/1995 | Bühlmayer et al. |
| 6,294,197 B1 | 9/2001 | Wagner et al. |
| 6,395,728 B2 | 5/2002 | Webb et al. |
| 6,485,745 B1 | 11/2002 | Wagner et al. |
| 6,858,228 B2 | 2/2005 | Katakuse et al. |
| 2005/0222137 A1 | 10/2005 | Shetty et al. |
| 2008/0171086 A1 * | 7/2008 | Joshi et al. ..................... 424/474 |

FOREIGN PATENT DOCUMENTS

| | | | |
|---|---|---|---|
| WO | WO 03/097045 A1 * | 11/2003 | ......... A61K 31/4184 |
| WO | WO 2007/022113 A2 | 2/2007 | |
| WO | WO 2007/085399 A1 | 8/2007 | |

OTHER PUBLICATIONS

EXFORGE® Tablet Label, Feb. 2007.

* cited by examiner

*Primary Examiner* — My-Chau T Tran
(74) *Attorney, Agent, or Firm* — Merchant & Gould P.C.

(57) ABSTRACT

A single layer pharmaceutical composition comprising active agent(s) amlodipine or a pharmaceutically acceptable salt thereof and valsartan or a pharmaceutically acceptable salt thereof wherein the composition exhibits bioequivalence to the commercially available bilayer tablet dosage form comprising amlodipine besylate and valsartan; when administered to human subject, under the bioequivalence parameters of a 90% Confidence Interval for AUC which is between 80% and 125%, and a 90% Confidence Interval for Cmax, which is between 80% and 125%.

11 Claims, No Drawings

PHARMACEUTICAL COMPOSITIONS OF AMLODIPINE AND VALSARTAN

This application is a National Stage Application of PCT/IN2008/000103, filed Feb. 21, 2008, which claims benefit of Serial No. 1449/KOL/2007, filed Dec. 31, 2007 in India and which applications are incorporated herein by reference. To the extent appropriate, a claim of priority is made to each of the above disclosed applications.

FIELD OF THE INVENTION

The present invention relates to single layer pharmaceutical compositions comprising amlodipine and valsartan or their pharmaceutically acceptable salts, hydrates, solvates or polymorphs or enantiomers and racemates thereof and a process of forming the same.

BACKGROUND OF THE INVENTION

Valsartan is an angiotensin II antagonist and is known to be effective in the treatment of congestive heart failure and reducing blood pressure irrespective of age, sex or race and is also well tolerated. It has also been approved to treat people after heart attacks.

U.S. Pat. No. 5,399,578 describes the preparation of valsartan and its pharmaceutically acceptable salt.

U.S. Pat. Nos. 4,879,303 and 4,572,909 describes the preparation of amlodipine and its pharmaceutically acceptable salt. The compound amlodipine (3-ethyl 5-methyl 2-(2-aminoethoxymethyl)-4-(2-chlorophenyl)-1,4-dihydro-6-methylpyridine-3,5-dicarboxylate) is a potent and long acting calcium channel blocker having utility as an anti-ischaemic and anti-hypertensive agent.

U.S. Pat. Nos. 6,294,197, 6,485,745 and 6,858,228 describe a solid oral dosage form of valsartan and optionally hydrochlorothiazide (HCTZ) prepared by compression method having more than 35% by weight based on total weight of the compressed solid oral dosage form, of the active ingredient.

U.S. Pat. No. 6,395,728 disclose combination of valsartan and amlodipine comprising from about 10 mg to about 200 mg of valsartan and 1 mg to about 180 mg amlodipine.

Combination of amlodipine and valsartan is marketed under the brand name EXFORGE® (amlodipine and valsartan) available in four different strengths: 5 mg/160 mg; 10 mg/160 mg; 5 mg/320 mg and 10 mg/320 mg. It is used for the treatment of hypertension.

WO 2007/022113 relates to monolayer and bilayer solid dosage forms of a combination of valsartan and amlodipine. This application discloses that for the 320 mg/5 mg fixed dose combination of valsartan and amlodipine it was not possible to get a bioequivalent product unless a bilayer tablet formulation was used.

As a person skilled in the art is aware, a bilayer tablet can exhibit certain disadvantages from many processing related limitations. Specialized machines are required for producing such tablets and the tablets are susceptible to bilayer separation. Moreover, the process of making bilayered tablets is less economical.

In light of this it was highly desirable to prepare a single layer composition of the combination product, which would also be bioequivalent to the bilayer tablet.

We have now surprisingly, found that it is possible to prepare a single layered pharmaceutical composition comprising amlodipine and valsartan or their pharmaceutically acceptable salts thereof, wherein the composition is bioequivalent to a tablet combination dosage form of amlodipine and valsartan marketed under the trade name of EXFORGE® (amlodipine and valsartan).

SUMMARY OF THE INVENTION

The aspect of the invention is to provide a single layer pharmaceutical composition comprising active agent(s)
  (a) amlodipine or a pharmaceutically acceptable salts thereof and
  (b) valsartan or a pharmaceutically acceptable salts thereof wherein: (i) the composition exhibits bioequivalence to the commercially available bilayer tablet dosage form comprising amlodipine besylate and valsartan; when administered to human subject, under the bioequivalence parameters of: (a) a 90% Confidence Interval for AUC which is between 80% and 125%, and (b) a 90% Confidence Interval for Cmax, which is between 80% and 125%.

Another aspect of the present invention is to provide a method of achieving bioequivalence between a single layer pharmaceutical composition comprising active agent(s)
  (a) amlodipine or a pharmaceutically acceptable salts thereof and
  (b) valsartan or a pharmaceutically acceptable salts thereof wherein: (i) the composition exhibits bioequivalence to the commercially available bilayer tablet dosage form comprising amlodipine besylate and valsartan; when administered to human subject, under the bioequivalence parameters of: (a) a 90% Confidence Interval for AUC which is between 80% and 125%, and (b) a 90% Confidence Interval for Cmax, which is between 80% and 125%.

Another aspect of the present invention is to provide a method of achieving bioequivalence between a single layer pharmaceutical composition comprising active agent(s)
  (a) amlodipine or a pharmaceutically acceptable salts thereof and
  (b) valsartan or a pharmaceutically acceptable salts thereof wherein: (i) the composition exhibits bioequivalence to the commercially available bilayer tablet dosage form comprising amlodipine besylate and valsartan; when administered to human subject, under the bioequivalence parameters of: (a) a 90% Confidence Interval for AUC which is between 80% and 125%, and (b) a 90% Confidence Interval for Cmax, which is between 80% and 125%, and iii) valsartan is present in an amount greater than 250 mg.

DETAILED DESCRIPTION OF THE INVENTION

The present invention relates to single layer pharmaceutical compositions comprising amlodipine and valsartan or their pharmaceutically acceptable salts, hydrates, solvates or polymorphs or enantiomers and racemates thereof and a process of forming the same which is bioequivalent to the commercially available bilayer tablet dosage form comprising amlodipine besylate and valsartan.

The "commercially available bilayer tablet dosage form comprising amlodipine besylate and valsartan" is EXFORGE® (amlodipine and valsartan). The bilayer tablet strengths are 10 mg/320 gm and 5 mg/320 mg of amlodipine besylate and valsartan.

In the pharmaceutical composition according to the invention, the active agent(s) comprises valsartan which includes its pharmaceutically acceptable salts, hydrates, solvates or polymorphs or enantiomers and racemates thereof in amount of about 250 mg to about 640 mg e.g. 320 mg, and amlodipine which includes its pharmaceutically acceptable salts, hydrates, solvates or polymorphs or enantiomers and racemates thereof. Especially preferred is the besylate salt.

In an embodiment of the present invention the pharmaceutical composition comprises active agent(s) in an amount less than about 35% by weight, based on the total weight of the pharmaceutical composition.

In another embodiment of the present invention the pharmaceutical composition comprises valsartan in an amount less than about 35% by weight, based on the total weight of the pharmaceutical composition.

The determination of the dose of the active agent(s) necessary to achieve the desired therapeutic effect is within the skill of those who practice in the art. The dose depends on the warm-blooded animal species, the age and the individual condition and on the manner of administration. In the normal case, an approximate daily dose in the case of oral administration for a patient weighing approximately 75 kg for oral application is of about 10 mg to about 320 mg, especially about 20 to about 120 mg, most preferably about 40 mg to about 80 mg for valsartan and about 1.0 mg to about 180 mg, preferably about 2.5 mg to about 50 mg, for the CCB, depending on the specific CCB. The exact dose of active agent(s) and the particular formulation to be administered depends on a number of factors, e.g. the condition to be treated, the desired duration of the treatment and the rate of release of the active agent. For example, the amount of the active agent required and the release rate thereof may be determined on the basis of known in vitro or in vivo techniques, determining how long a particular active agent concentration in the blood plasma remains at an acceptable level for a therapeutic effect.

The combination therapy with valsartan and a calcium channel blocker results in a more effective antihypertensive therapy through improved efficacy as well as a greater responder rate.

The active may further comprises another active agent selected from the group comprising, but are not limited to, other calcium channel blocker (CCB), AT II Antagonist, renin inhibitors an angiotensin converting enzyme (ACE) inhibitor, an aldosterone synthase inhibitor an aldosterone antagonist, a dual angiotensin converting enzyme/neutral endopetidase (ACE/NEP) inhibitor, an endothelin antagonist, alpha and beta adrenergic blockers, HMG CoA reductase inhibitors and a diuretic or their pharmaceutically acceptable salts, hydrates, solvates or polymorphs or enantiomers and racemates thereof.

"Pharmaceutical composition" includes granules, pellets or those in unit dose forms such as tablets, capsules and the like, and furthermore ampoules and the like; prepared by methods well known to a person skilled in the art. Thus, pharmaceutical preparations for oral use can be obtained by combining the active agent(s) with solid carriers, if desired granulating a mixture obtained, and processing the mixture or granules, if desired or necessary, after addition of suitable or pharmaceutically acceptable excipients to give tablets.

The term "single layer" as per the invention includes solid oral dosage forms wherein both the actives are present together either as coated or uncoated dosage forms preferably tablets. The coated or uncoated dosage forms can be prepared in various sizes and shapes as appreciated by the person skilled in the art. The above dosage forms can also made as mini tablets which can further be filled into capsule shells.

The term single layer specifically excludes solid oral dosage forms wherein both the actives are present separately as bilayered tablets.

The pharmaceutically acceptable excipients or additives include but are not limited to disintegrants, binders, lubricants, glidants, fillers, diluents and the like.

The amounts of additive employed will depend upon how much active agent is to be used. One excipient can perform more than one function. The absolute amount of additives and the amounts relative to other additives are also dependent on the desired properties of the pharmaceutical composition and may also be chosen by the skilled artisan by routine experimentation without undue burden.

Disintegrants, include but are not limited to, cross linked polyvinylpyrrolidone (crospovidone, polyplasdone, kollidon XL); starches such as modified starches, pregelatinized starch, maize starch, pregelatinized starch, dried starch and sodium starch glycolate; gum such as alginic acid, sodium alginate, guar gum; croscarmellose sodium, cellulose products such as microcrystalline cellulose and its salts, microfine cellulose, low substituted hydroxypropylcellulose and mixtures thereof; ion exchange resins like polacrilin potassium; most preferably crosslinked polyvinylpyrrolidone, crospovidone, crosslinked carboxymethylcellulose.

Binders include, but are not limited to, starches such as potato starch, wheat starch, corn starch; microcrystalline cellulose such as products known under the registered trade marks Avicel, Filtrak, Heweten or Pharmacel; celluloses such as hydroxypropyl cellulose, hydroxyethyl cellulose, hydroxypropylmethyl cellulose, ethyl cellulose, sodium carboxy methyl cellulose; natural gums like acacia, alginic acid, guar gum; liquid glucose, dextrin, povidone, syrup, polyethylene oxide and mixtures thereof.

Lubricants may be selected from, but are not limited to, those conventionally known in the art such as Mg, Al or Ca or Zn stearate, polyethylene glycol, glyceryl behenate, mineral oil, sodium stearyl fumarate, stearic acid, hydrogenated vegetable oil and talc.

Glidants include, but are not limited to, silicon dioxide; magnesium trisilicate, powdered cellulose, starch, talc and tribasic calcium phosphate.

Fillers or diluents, which include, but are not limited to confectioner's sugar, compressible sugar, dextrates, dextrin, dextrose, fructose, lactitol, mannitol, sucrose, starch, lactose, xylitol, sorbitol, talc, microcrystalline cellulose, calcium carbonate, calcium phosphate dibasic or tribasic, calcium sulphate, and the like can be used.

One or more of these additives can be selected and used by the skilled artisan having regard to the particular desired properties of the solid oral dosage form. The amount of each type of additive employed, e.g. glidant, binder, disintegrant, filler or diluent and lubricant may vary within ranges conventional in the art.

The pharmaceutical composition of the invention, wherein the core can be formed by various methods known in the art such as by dry granulation, wet granulation, direct compression, extrusion spheronization, layering and the like;

The pharmaceutical composition of the invention can be prepared for oral administration to mammals (warm-blooded animals), including man, comprising a therapeutically effective amount of the pharmacologically active compound(s), alone or in combination with one or more pharmaceutically acceptable carries, especially suitable for.

The invention provides in another of its aspects a process of making a pharmaceutical composition as hereinabove described. Such pharmaceutical compositions may be produced by working up components a) amlodipine b) valsartan and c) pharmaceutically acceptable additive(s) defined hereinabove in appropriate amounts, to form unit dosage forms.

In a preferred embodiment, there is provided a process of making a pharmaceutical composition as hereinabove described comprising the steps of i) blending the active agents with pharmaceutically acceptable additives,
ii) subjecting the blend to slugging/compaction to form a compacted mass
iii) sifting the compacted mass to form granules and
iv) compressing the granules to form the solid oral dosage form.

Compaction of the blend into compacted mass may be carried out using a slugging technique or preferably, roller compaction. The milling of the granules may be carried out according to conventional milling methods. The compression of the granulates to tablet cores can be carried out in a conventional tabletting machine, eccentric tabletting machine or a rotary compression machine.

The tablets may further be coated by using any of the conventional coating techniques, such as pan or perforated pan, well known to the persons skilled in the art.

These coating layers comprise of one or more excipients selected from the group comprising coating agents, opacifiers, taste-masking agents, colouring agents, antitacking agents and the like.

Coating agents which are useful in the coating process, include, but are not limited to, polysaccharides such as maltodextrin, alkyl celluloses such as methyl or ethyl cellulose, hydroxyalkylcelluloses (e.g. hydroxypropylcellulose or hydroxypropylmethylcelluloses); polyvinylpyrrolidone, polyvinyl alcohol, copolymers of vinylpyrrolidone and vinyl acetate (e.g. marketed under the brand name of Plasdone) and polymers based on methacrylic acid such as those marketed under the brand name of Eudragit. These may be applied from aqueous or non-aqueous systems or combinations of aqueous and non-aqueous systems as appropriate. Additives can be included along with the film formers to obtain satisfactory films. These additives can include plasticizers such as dibutyl phthalate, triethyl citrate, polyethylene glycol and the like, antitacking agents such as talc, stearic acid, magnesium stearate and colloidal silicon dioxide and the like, surfactants such as polysorbates and sodium lauryl sulphate and opacifying agents such as titanium dioxide and the like. All these excipients can be used at levels well known to the persons skilled in the art.

While the foregoing specification teaches the principles of the present invention, with examples provided for the purpose of illustration, it will be understood that the practice of the invention encompasses all of the casual variations, adaptations, modifications, deletions or additions of procedures and protocols described herein, as come within the scope of the following claims and its equivalents.

EXAMPLES

Example 1 & 2

Amlodipine and Valsartan Tablets

|  | % w/w | |
|---|---|---|
| Ingredient | Example 1: 10/320 | Example 2: 5/320 |
| Valsartan | 30.42 | 30.42 |
| Amlodipine besylate | 1.32 | 0.66 |
| Microcrystalline Cellulose | 58.13 | 58.79 |
| Crospovidone | 5.71 | 5.71 |
| Colloidal Silicone Dioxide | 1.99 | 1.99 |
| Magnesium Stearate NF | 1.19 | 1.09 |

-continued

|  | % w/w | |
|---|---|---|
| Ingredient | Example 1: 10/320 | Example 2: 5/320 |
| Croscarmellose Sodium USP | 1.24 | 1.24 |
| Film Coating | Q.S. | Q.S. |

Brief Manufacturing Process
1. The sifted components except a part of microcrystalline cellulose, crosslinked polyvinylpyrrolidone and colloidal silicon dioxide are blended in a suitable blender.
2. Mixed Amlodipine with step 1 material geometrically and & sifted through appropriate sieve
3. Sifted magnesium stearate through appropriate sieve and lubricated step 2 material.
4. The blended material is compacted to form slugs/compacts.
5. The compacted mass is milled and sieved again to form granules. The remaining portion of the microcrystalline cellulose, crospovidone, colloidal silicon dioxide, croscarmellose silicon dioxide are added and blended in a suitable blender.
6. The prepared granules are lubricated and compressed into the tablets.
7. The tablets are then coated using film coating composition.

Bioequivalence Study

The test composition was prepared according to example 1 and was evaluated against EXFORGE® (amlodipine and valsartan) having 10 mg amlodipine besylate and 320 mg of Valsartan, by Novartis, as reference.

An open label, balanced, randomized, two treatment, two sequence, two-period, crossover oral bioequivalence study was carried out in 51 healthy human volunteers. Each received single dose of 10 mg of amlodipine besylate and 320 mg of valsartan in fasted state. 47 healthy volunteers received single dose of 10 mg of amlodipine besylate and 320 mg of valsartan in fed state.

The study was monitored in terms of the AUC and $C_{max}$ achieved with the test product and reference product. AUCs are areas under plasma concentration of valsartan—time curves or amlodipine-time curves. Generally, the values for AUC represent a number of values taken from all the subjects in a population and are, therefore, mean values averaged over the entire population. $C_{max}$, the observed maximum plasma concentration of valsartan or amlodipine is likewise an average value. The ratios of the log transformed mean values for $C_{max}$ and AUC for the test and reference product (T/R ratio) is a measure of the bioequivalence between the test and reference product. Values between 80 and 125% for these intervals indicate bioequivalence as recommended by the US FDA.

Bioequivalence data for composition containing amlodipine and valsartan against the commercially available tablets EXFORGE® (amlodipine and valsartan) is shown below in Tables 1, 2, 3 and 4.

Surprisingly, we have found that single layered pharmaceutical composition comprising active agent(s) amlodipine besylate and valsartan exhibits bioequivalence to the commercially available bilayer tablet, EXFORGE® (amlodipine and valsartan); when administered to human subject, under the bioequivalence parameters of: (a) a 90% Confidence Interval (CI) for AUC which is between 80% and 125%, and (b) a 90% Confidence Interval for Cmax, which is between 80% and 125%.

TABLE 1

Fed BE study data of Amlodipine against
commercially available tablets Exforge ®
(amlodipine and valsartan); n = 47

| PK Parameters | Geometric Mean Plasma Concentration | Log Transformed T/R (%) of Geometric Least Square Mean | CI 90% on Log Transformed data |
|---|---|---|---|
| $C_{max}$ | 5.5231 ng/ml | 94.44 | 0.962-0.984 |
| $AUC_{(0-t)}$ | 346.6522 ng.hr/ml | 96.78 | 0.917-1.027 |
| $AUC_{(0-\infty)}$ | 376.0003 ng.hr/ml | 97.48 | 0.918-1.034 |

TABLE 2

Fed BE study data of Valsartan against
commercially available tablets Exforge ®
(amlodipine and valsartan); n = 47

| PK Parameters | Geometric Mean Plasma Concentration | Log Transformed T/R (%) of Geometric Least Square Mean | CI 90% on Log Transformed data |
|---|---|---|---|
| $C_{max}$ | 6173.4059 ng/ml | 103.62 | 0.972-1.104 |
| $AUC_{(0-t)}$ | 49733.7888 ng.hr/ml | 104.27 | 0.979-1.110 |
| $AUC_{(0-\infty)}$ | 51727.6142 ng.hr/ml | 104.74 | 0.983-1.115 |

TABLE 3

Fasted BE study data of Amlodipine against commercially
available tablets Exforge ®
(amlodipine and valsartan) n = 51

| PK Parameters | Geometric Mean Plasma Concentration | Log Transformed T/R (%) of Geometric Least Square Mean | CI 90% on Log Transformed data |
|---|---|---|---|
| $C_{max}$ | 5.3728 ng/ml | 96.00 | 0.917-1.004 |
| $AUC_{(0-t)}$ | 315.1817 ng.hr/ml | 96.72 | 0.909-1.028 |
| $AUC_{(0-\infty)}$ | 337.1193 ng.hr/ml | 96.63 | 0.910-1.025 |

TABLE 4

Fasted BE study data of Valsartan against commercially
available tablets Exforge ®
(amlodipine and valsartan) n = 51

| PK Parameters | Geometric Mean Plasma Concentration | Log Transformed T/R (%) of Geometric Least Square Mean | CI 90% on Log Transformed data |
|---|---|---|---|
| $C_{max}$ | 7027.7017 ng/ml | 94.34 | 0.873-1.019 |
| $AUC_{(0-t)}$ | 45779.3115 ng.hr/ml | 91.59 | 0.856-0.979 |
| $AUC_{(0-\infty)}$ | 46983.5253 ng.hr/ml | 91.27 | 0.854-0.975 |

$C_{max}$ = Maximum plasma concentration
$AUC_{(0-t)}$ = Area under the plasma concentration time curve from time 0 to t
$AUC_{(0-\infty)}$ = Area under the plasma concentration time curve from time 0 to ∞

The invention claimed is:

1. A single layer pharmaceutical composition comprising active agent(s)
   (a) amlodipine or a pharmaceutically acceptable salt thereof and
   (b) valsartan or a pharmaceutically acceptable salt thereof
   wherein:
   (i) the composition exhibits bioequivalence to the commercially available bilayer tablet dosage form comprising amlodipine besylate and valsartan; when administered to a human subject, under the bioequivalence parameters of: (a) a 90% Confidence Interval for AUC which is between 80% and 125%, and (b) a 90% Confidence Interval for Cmax, which is between 80% and 125%; and
   (ii) wherein valsartan is present in an amount less than 35% by weight, based on the total weight of the pharmaceutical composition.

2. A single layer pharmaceutical composition according to claim 1, wherein valsartan is present in a unit dose in amount ranging from about 250 mg to about 640 mg.

3. A single layer pharmaceutical composition according to claim 1, wherein active agent is present in an amount less than 35% by weight, based on the total weight of the pharmaceutical composition.

4. A single layer pharmaceutical composition according to claim 1, comprising pharmaceutically acceptable additives selected from the group comprising fillers or diluents, binders, lubricants, glidants and disintegrants.

5. A single layer pharmaceutical composition of claim 4, wherein the diluent is one or more selected from the group comprising confectioner's sugar, compressible sugar, dextrates, dextrin, dextrose, lactitol, fructose, mannitol, sucrose, starch, lactose, dibasic or tribasic calcium phosphate, calcium carbonate, calcium sulphate, xylitol, sorbitol, talc, microcrystalline cellulose or mixtures thereof.

6. A single layer pharmaceutical composition claim 4, wherein the binder is one or more selected from the group comprising methyl cellulose, hydroxypropylcellulose, low substituted hydroxypropylcellulose, hydroxypropyl methylcellulose, sodium carboxymethylcellulose, ethyl cellulose, microcrystalline cellulose, potato starch, wheat starch, corn starch, pregelatinised maize starch, polyvinylpyrrolidone, acacia, alginic acid, guar gum; liquid glucose, dextrin, povidone, syrup, polyethylene oxide and mixtures thereof.

7. A single layer pharmaceutical composition of claim 4, wherein the lubricant is one or more selected from the group comprising Mg, Al, Zn or Ca stearate, polyethylene glycol, mineral oil, sodium stearyl fumarate, stearic acid, hydrogenated vegetable oil, glyceryl behenate, talc and mixtures thereof.

8. A single layer pharmaceutical composition of claim 4, wherein the glidant is one or more selected from the group comprising silicon dioxide, colloidal silica, powdered cellulose, talc, tribasic calcium phosphate and mixtures thereof.

9. A single layer pharmaceutical composition of claim 4, wherein the disintegrant is one or more selected from the group comprising cross linked polyvinylpyrrolidone, maize starch, dried starch, pregelatinized starch, sodium starch glycolate, alginic acid, sodium alginate, guar gum, croscarmellose sodium, microcrystalline cellulose and its salts, microfine cellulose, low substituted hydroxypropylcellulose, ion exchange resins and mixtures thereof.

10. A pharmaceutical composition described in claim 1, which is in the form of tablets, capsules, granules, microparticles, minitablets and pellets.

11. A pharmaceutical composition of claim 1 is further coated.

* * * * *